(12) United States Patent
Ho et al.

(10) Patent No.: US 7,726,309 B2
(45) Date of Patent: Jun. 1, 2010

(54) FLEXIBLE CONNECTOR

(75) Inventors: Peter Chi Fai Ho, Pittsburgh, PA (US);
Jerome Matula, Jr., Apollo, PA (US);
Lance Busch, Trafford, PA (US);
Derrick Andrews, Markleton, PA (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 11/809,940

(22) Filed: Jun. 4, 2007

(65) Prior Publication Data
US 2007/0277828 A1 Dec. 6, 2007

Related U.S. Application Data

(60) Provisional application No. 60/811,006, filed on Jun. 5, 2006.

(51) Int. Cl.
*A61M 11/00* (2006.01)
(52) U.S. Cl. .................. 128/204.18; 128/912
(58) Field of Classification Search ........... 128/204.18, 128/206.21, 207.13, 205.11, 207.18, 206.12, 128/912, 205.25
See application file for complete search history.

(56) References Cited
U.S. PATENT DOCUMENTS

| | | | | |
|---|---|---|---|---|
| 1,926,027 | A * | 9/1933 | Biggs | 128/205.25 |
| 3,388,705 | A * | 6/1968 | Grosshandler | 128/207.14 |
| 4,340,089 | A * | 7/1982 | Freiherr von Arnim et al. | 138/121 |
| 4,846,510 | A * | 7/1989 | Mikol | 285/226 |
| 4,852,564 | A * | 8/1989 | Sheridan et al. | 128/202.27 |
| 4,921,147 | A * | 5/1990 | Poirier | 222/527 |
| 5,357,945 | A * | 10/1994 | Messina | 128/200.14 |
| 5,438,981 | A | 8/1995 | Starr et al. | |
| 5,647,355 | A | 7/1997 | Starr et al. | |
| 6,039,044 | A | 3/2000 | Sullivan | |
| 6,491,034 | B1 | 12/2002 | Gunaratnam et al. | |
| 6,561,191 | B1 | 5/2003 | Kwok | |
| 6,595,214 | B1 * | 7/2003 | Hecker et al. | 128/207.13 |
| 6,615,830 | B1 | 9/2003 | Serowski et al. | |
| 6,691,707 | B1 | 2/2004 | Gunaratnam et al. | |
| 6,851,425 | B2 | 2/2005 | Jaffre et al. | |
| 7,320,323 | B2 * | 1/2008 | Lang et al. | 128/206.24 |
| 2003/0005931 | A1 | 1/2003 | Jaffre et al. | |

* cited by examiner

*Primary Examiner*—Steven O Douglas
(74) *Attorney, Agent, or Firm*—Michael W. Haas

(57) ABSTRACT

A flexible connector that couples a delivery conduit to a patient interface device and a pressure support system that includes such a flexible connector. The flexible connector of the present invention prevents disruption of the seal between the patient interface and the patient's face. The flexible connector may have a bellows portion with a longitudinally directed portion, a narrowed neck portion, or a plurality of corrugations. The flexible connector may further have a swivel portion and/or an exhaust member, and/or a hinge member.

26 Claims, 10 Drawing Sheets

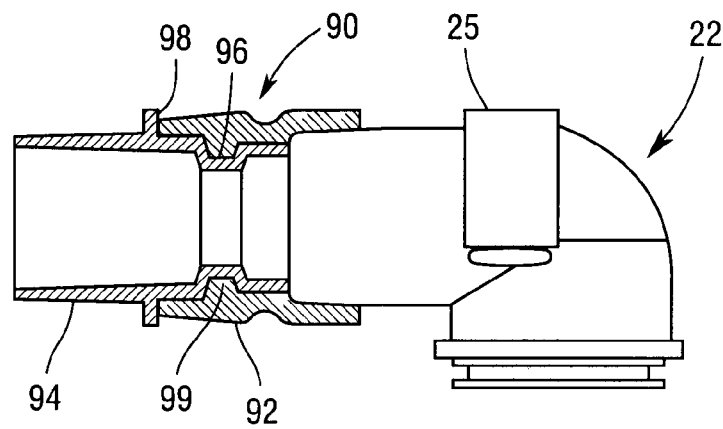
*Fig.9*
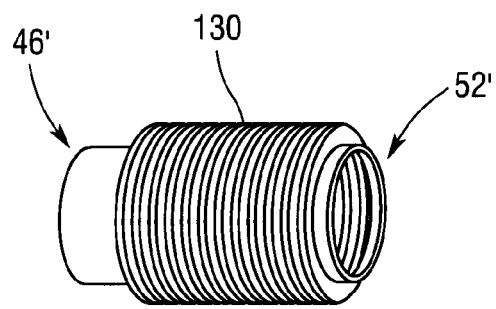 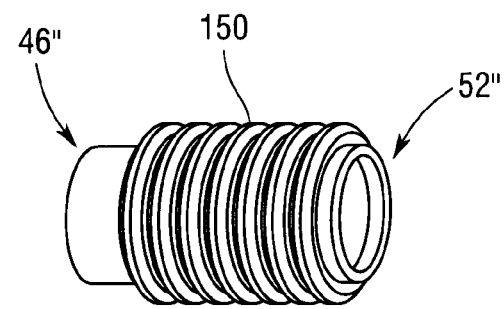
*Fig.13*         *Fig.15*
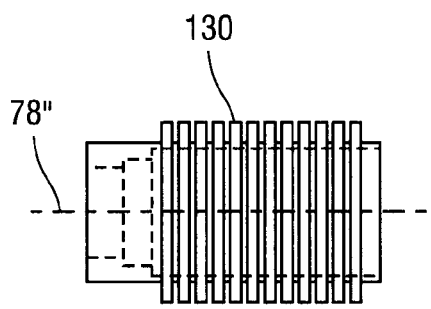 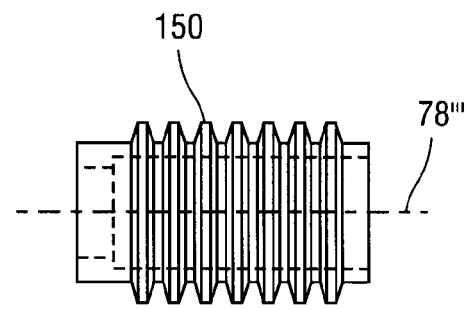
*Fig.14*         *Fig.16*

FLEXIBLE CONNECTOR

CROSS-REFERENCE TO RELATED APPLICATIONS

This application claims priority under 35 U.S.C. §119(e) from provisional U.S. patent application No. 60/811,006 filed Jun. 5, 2006 the contents of which are incorporated herein by reference.

BACKGROUND OF THE INVENTION

1. Field of the Invention

The present invention generally relates to a connector for use in a pressure support system that supplies a flow of gas to the airway of a patient, and, in particular, to a flexible connector that couples a delivery conduit to a patient interface device and to a pressure support system that includes such a flexible connector.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), or congestive heart failure.

As used herein, the phrases "pressure support system", "pressure support device", "positive pressure support", and derivatives thereof, include any medical device or method that delivers a flow of breathing gas to the airway of a patient, including, but not limited to, a ventilator, CPAP, PAV, PPAP, or bi-level pressure support system.

Non-invasive ventilation and pressure support therapies involve the placement of a patient interface device, which typically includes a nasal or nasal/oral mask, on the face of a patient to interface a pressure support system with the airway of the patient so that a flow of breathing gas can be delivered from a pressure/flow generating device to the airway of the patient. Generally, the flow of breathing gas is delivered via a delivery conduit or patient circuit which connects the pressure/flow generating device to the mask. A headgear may be employed to maintain the mask on the face of a patient.

Because such masks are typically worn for an extended period of time, a variety of concerns must be taken into consideration. For example, in providing CPAP to treat OSA, the patient normally wears the patient interface device all night long while he or she sleeps. One concern in such a situation is that movement of the delivery conduit will disrupt the seal which is formed between the mask and the patient's face. Prior art connectors fail to provide the flexibility necessary to account for this movement. Accordingly, there is a need for a connector that provides increased and freer movement between the mask and the delivery conduit.

SUMMARY OF THE INVENTION

Accordingly, the present invention provides a flexible connector for a pressure support system that addresses the above-identified concerns and that overcomes shortcomings of conventional connectors and/or patient interface devices. The flexible connector of the present invention prevents disruption of the seal between the patient interface device and the patient's face. The flexible connector may have a swivel portion. The flexible connector may have a bellows portion with a longitudinally directed portion, a narrowed neck portion, or a plurality of corrugations. The present invention further provides a system for delivering a flow of gas to a patient that addresses the above identified concerns and that does not suffer from the shortcomings of conventional systems. This is achieved by providing a system for delivering a flow of gas to a patient that includes a gas flow generating device capable of producing a flow of gas and a conduit having a first end portion operatively coupled to the gas flow generating device and a second end portion. The conduit carries the flow of gas from the gas flow generating device. The system includes a patient interface device operatively coupled to the second end portion of the conduit via a flexible connector. The patient interface device may be a nasal mask assembly, an oral mask, or mouthpiece, or combination nasal/oral masks.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 9 is a cross-sectional view of a connector according to the principles of another embodiment of the present invention connected to a mask elbow.

FIGS. 13 and 14 illustrate an alternate configuration for a flexible coupling for a connector of the present invention.

FIGS. 15 and 16 illustrate an alternate configuration for a flexible coupling for a connector of the present invention.

DETAILED DESCRIPTION OF THE EXEMPLARY EMBODIMENTS

Figure 1:
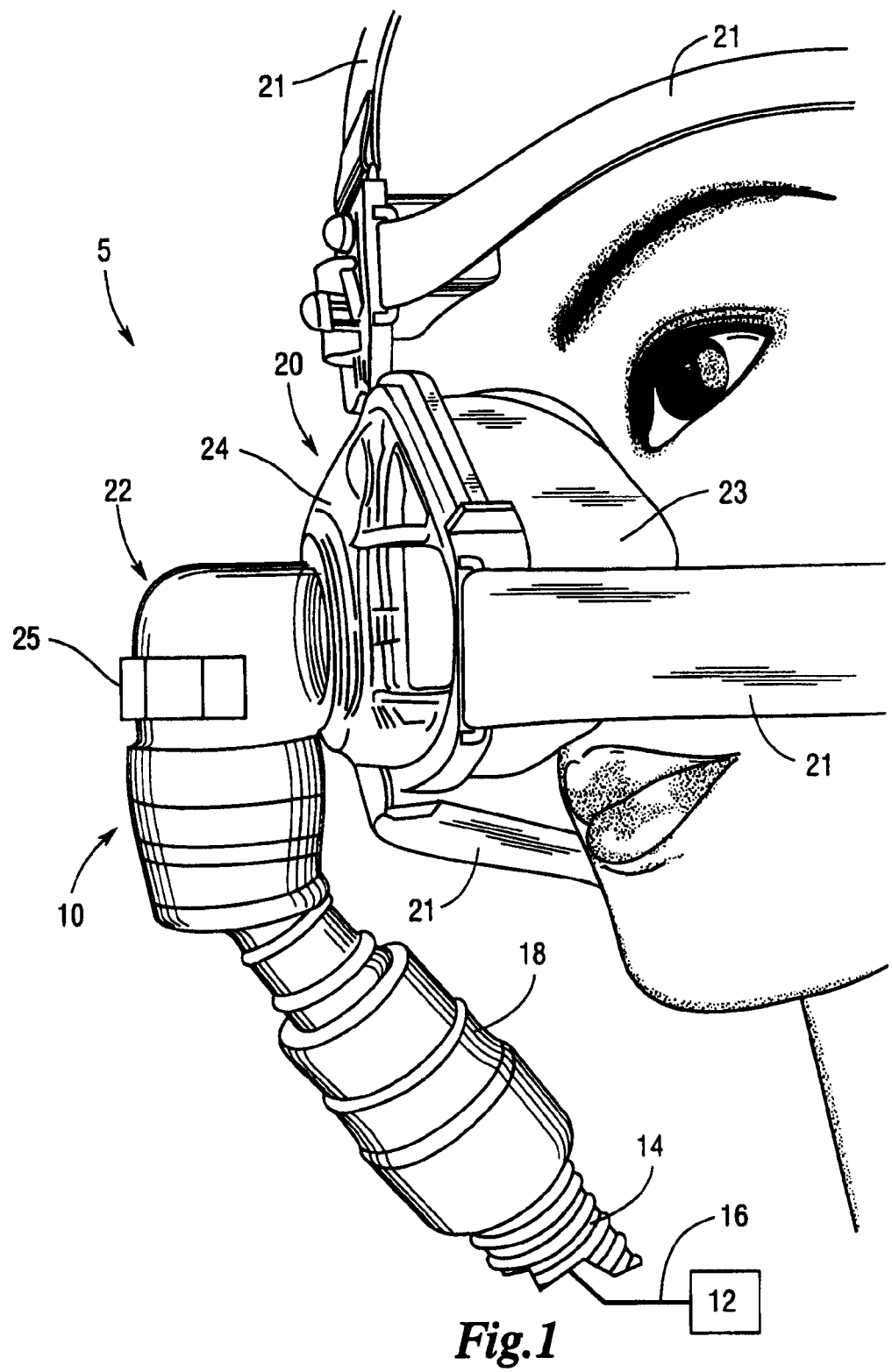
FIG. 1 illustrates a system for delivering a flow of gas to a patient according to the principles of one embodiment of the present invention.

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

FIG. 1 illustrates an exemplary embodiment of a system 5 for delivering pressurized breathing gas to a patient. System 5 includes a pressure generating device 12, a conduit 14, a connector 10, and a patient interface device 20. Pressure generating device 12 (shown schematically) is structured to produce a flow of gas. Conduit 14, which may also be referred to as a patient circuit, has a first end portion 16 operatively coupled to pressure generating device 12 and a second end portion 18 coupled to patient interface device 20 via connector 10. During operation of the system, the flow of gas generated by pressure generating device 12 flows through conduit 14, connector 10, and patient interface device 20 and is delivered to the airway of the patient.

Pressure/flow generating device 12 is any conventional ventilator, pressure support system, or other device that is used to communicate a flow of gas at an elevated pressure above the ambient pressure to the airway of the user. Examples of such systems include, but are not limited to: a ventilator, continuous positive airway pressure (CPAP) device, or a variable pressure device, e.g. an auto-titrating device, proportional assist ventilation (PAV®) device, proportional positive airway pressure (PPAP®) device, C-Flex™ device, Bi-Flex™ device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device. Other devices that communicate a flow of gas with an airway of a patient suitable for use in with the present invention include devices that apply a high and low or positive and negative pressure to the airway for purposes of secretion clearance or loosening. For present purposes, pressure generating device 12 is also referred to as a gas flow generating device, because flow results when a pressure gradient is generated. Communicating a flow of breathing gas between the patient's airway and pressure generating device 12 includes delivering a flow of breathing gas to the patient from pressure generating device 12 and exhausting a flow of gas from the patient to ambient atmosphere.

Patient interface device 20 may be, for example, a nasal mask, an oral mask, or a mouthpiece, or a combination of nasal/oral masks. Patient interface device 20 shown in FIG. 1 is a nasal mask having a mask shell 24 coupled to a cushion 23. Cushion 23 is structured to create a seal between the patient interface device 20 and the patient's face. The embodiment illustrated in FIG. 1 includes an L-shaped conduit or mask elbow 22 rotatably connected to the mask shell 24. The combination of patient interface device 20 and elbow 22 may be referred to as a patient interface assembly. The patient interface assembly may include an exhaust member 25, which as illustrated in FIG. 1, is located on mask elbow 22. The specific exhaust member 25 and its location may be varied while remaining within the scope of the present invention. A headgear (only a portion of which is shown in FIG. 1) with a number of straps 21 may be used to secure patient interface device 20 to the patient's head. It is to be understood that other accessories used in a pressure support system, such as a humidifier, heater, pressure sensor, flow sensor, temperature sensor, humidity sensor, bacteria filter, etc. can be used in conjunction with the patient interface device of the present invention. The present invention contemplates that patient interface device 20 is any device adapted to communicate the flow of gas from the patient circuit to the airway of the user, such as a nasal mask that seals around the patient's nares. Examples of other patient interface devices include, but are not limited to, nasal pillows or prong that insert or seal each nare, a nasal/oral mask, a full face or total mask, a hood, a tracheal tube, an endotracheal tube.

Movement of conduit 14 relative to patient interface 20 may cause forces to be generated which, when applied to the patient interface device 20, may have a negative impact upon the seal created between the cushion 23 and the patient's face. Connector 10 of the present invention (as well as the other connectors of the present invention discussed herein) is structured to eliminate or reduce the application of these forces to the patient interface device 20. Accordingly, connector 10 of the present invention (as well as the other connectors of the present invention discussed herein) is structured to help maintain the seal between the cushion 23 and the patient's face.

Figure 2:
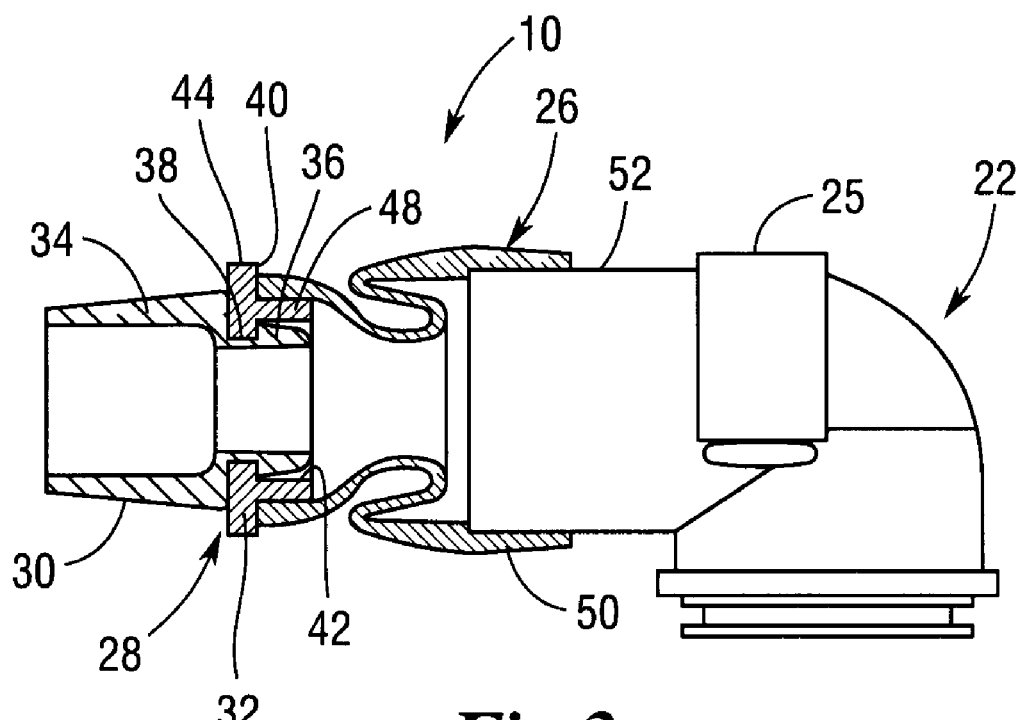
FIG. 2 is a cross-sectional view of a connector according to the principles of one embodiment of the present invention coupled with a mask elbow.
Figure 3:
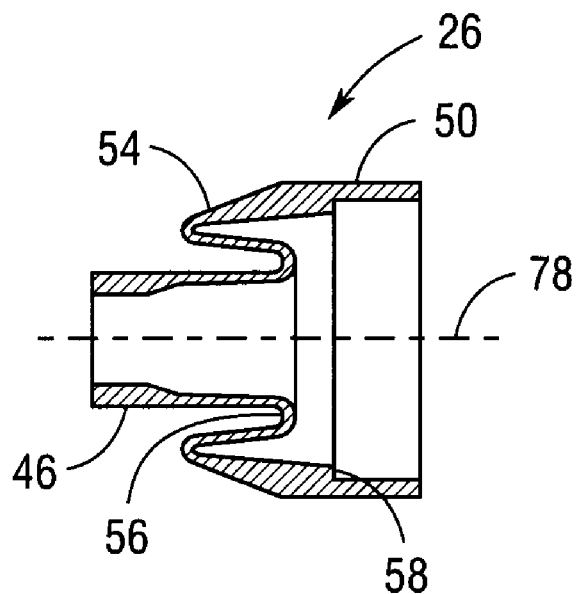
FIG. 3 is a cross-sectional view of the flexible coupling of FIG. 2.

Connector 10 is illustrated in FIGS. 2-5. Connector 10 is structured to connect conduit 14 to mask elbow 22 (FIG. 1). Referring to FIGS. 2 and 3, connector 10 has a three-piece design including a flexible coupling or mask connection portion 26 which is connectable to elbow 22, and a two-piece swivel connector 28 which is connectable to delivery conduit 14. Swivel connector 28 includes a delivery conduit portion 30 which is receivable within delivery conduit 14, and a swivel adapter 32 which is rotatably connected to delivery conduit portion 30 and non-rotatably connected to mask connection portion 26. As shown in FIG. 1, delivery conduit 14 is non-rotatably friction fit over delivery conduit portion 30. Delivery conduit portion 30 has a larger diameter end portion 34 and a smaller diameter end portion 36. Larger diameter end portion 34 is connectable with delivery conduit 14. Smaller diameter end portion 36 has a locating swivel groove 38 on the exterior thereof disposed near larger diameter end portion 34. Swivel adapter 32 includes a shoulder portion 40 having an interior portion 42 which is receivable in locating swivel groove 38, and an exterior portion 44 forming a shoulder step for locating a swivel connection end 46 (FIG. 3) of mask connection portion 26. Swivel adapter 32 further includes a generally cylindrical portion 48.

Flexible coupling or mask connection portion 26 has a mask connection end 50 which, in the embodiment illustrated in FIG. 2, is structured to non-rotatably couple with elbow 22. Mask connection end 50 includes an interior step 58 for locating connection end 52 of elbow 22. Swivel connection end 46 of mask connection portion 26 is structured to non-rotatably coupled with swivel connector 28. In the illustrated embodiment, mask connection end 50 is stretch fit over a connection end 52 of elbow 22. Swivel connection end 46 is stretch fit over cylindrical portion 48 of swivel adapter 32 and located at exterior portion 44. Both swivel connection end 46 and mask connection end 50 have inner diameters that are smaller than the exterior diameters of cylindrical portion 48 or connection end 52, respectively, and may be glued or mechanically locked thereto. Although shown connected to elbow 22 in the current embodiment, it is contemplated that connector 10 may be adapted to connect to another fitting and/or adapted to directly connect to patient interface device 20 while remaining within the scope of the present invention.

As best seen in FIG. 3, mask connection portion 26 has a flexible portion 54 between swivel connection end 46 and mask connection end 50. Flexible portion 54 comprises an inward bellows portion 56 having a generally S-shaped cross-section. Bellows portion 56 has an inner bellows disposed in the longitudinal direction of mask connection portion 26. Bellows portion 56 is generally thinner than swivel connection end 46 and mask connection end 50.

Figure 4:
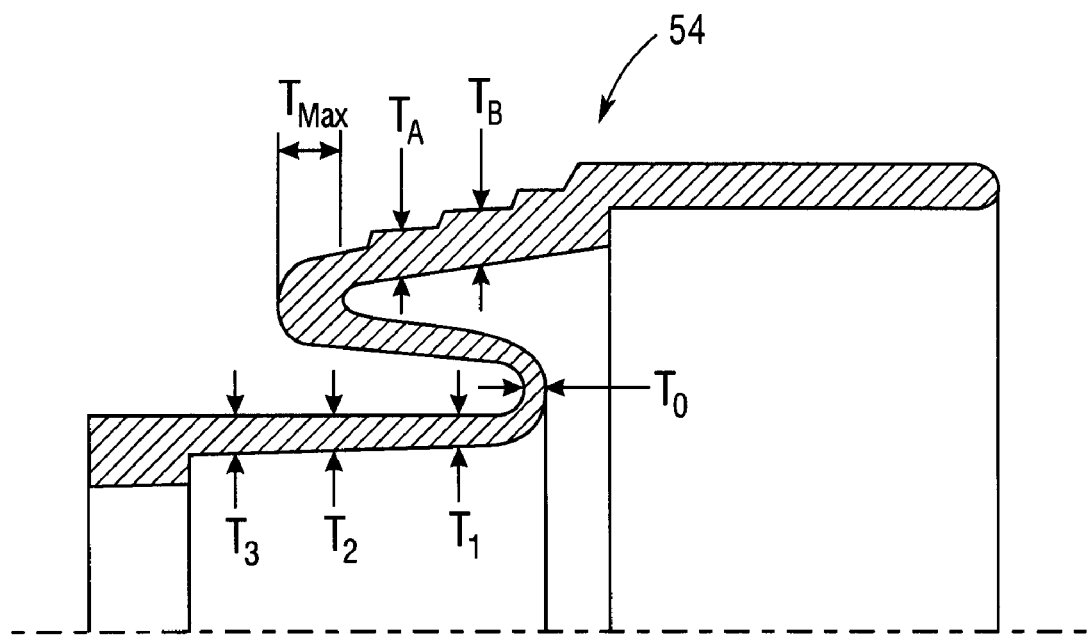
FIG. 4 is partial cross-sectional view of the flexible coupling of FIG. 2 showing thickness distribution.
Figure 5:
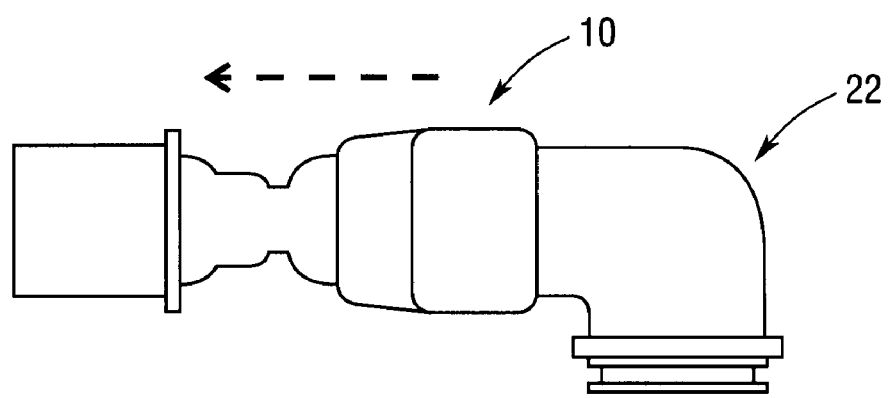
FIG. 5 is a side view of the pull-out position of the flexible coupling of the connector of FIG. 2 connected to the mask elbow.

The thickness distribution of flexible portion 54 is shown in FIG. 4. The thickness of flexible portion 54 gradually reduces from a maximum thickness at the outer portions of the S-shaped cross-section to minimum thickness at the lower interior curve of the S-shaped cross-section. For instance in the current embodiment, $T_B > T_A > T_3 > T_2 > T_1 > T_0$, where $T_0$ is a minimum thickness. The thickness distribution of flexible portion 54 is structured to help prevent "pull-out" which occurs when inner bellows pulls out completely as shown in FIG. 5. The thickness distribution also defines and restricts the flexible motion of mask connection portion 26. Bellows portion 56 allows flexing about the central axis 78 of the mask connection portion 26 and a small amount of controlled relative motion in a longitudinal direction. Mask connection portion 26 is preferably formed from an injection molding with TPE or liquid injection molding with silicone resulting in a moderate softness, approximately 60 Shore A for example. It is contemplated that the required material hardness may vary in relation to the wall thickness of flexible portion 54. For example, should the wall thickness of flexible portion 54 increase relative to the wall thickness of flexible portion 54 illustrated in FIG. 4, a softer material may be used. On the other hand, should the wall thickness of flexible portion 54 decrease relative to the wall thickness of flexible portion 54 illustrated in FIG. 4, a harder material may be used. Although flexible portion 54 has been discussed as being formed from a single material having various thicknesses, it is contemplated that more than one material, each having an associated thickness, may be used while remaining within the scope of the present invention.

Alternative exemplary embodiments of connectors according to the principles of the present invention are illustrated in FIGS. 6-22. In these embodiments, many features are similar to those illustrated in FIGS. 1-5. Thus, the description of each of these embodiments will focus primarily on the features unique to the embodiment of each connector. These alternative embodiments are provided primarily to show different possible configurations for a connector according to the principles of the present invention. It should be noted, however, that other configurations are possible and that mixing and matching of the features of the elements illustrated in all of these embodiments is contemplated.

Figure 6:
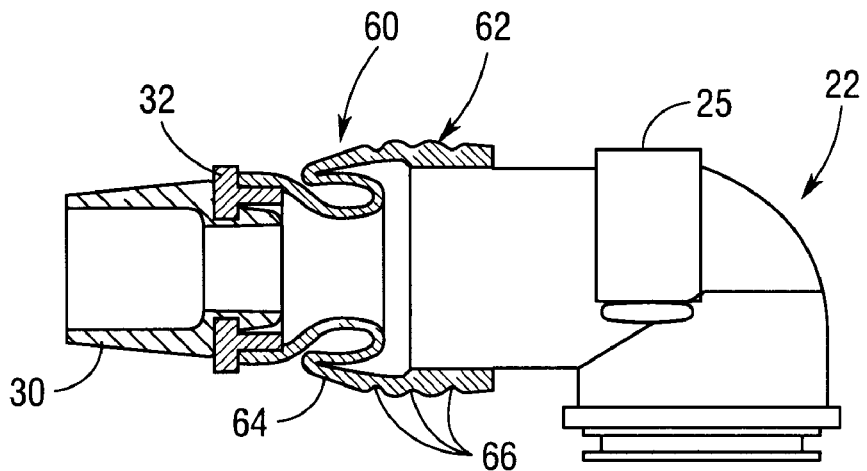
FIG. 6 is a cross-sectional view of a connector according to the principles of another embodiment of the present invention connected to a mask elbow.

In the embodiment illustrated in FIG. 6, connector 60 is similar to connector 10 that is illustrated in FIGS. 1-5. Mask connection end 62, however, of mask connection portion 64 has a plurality of grooves 66 on the exterior surface thereof for ease of gripping and for aesthetical purposes. Mask connection portion 64 is preferably formed from an injection molding with TPE or liquid injection molding with silicone resulting in a moderate softness, approximately 60 Shore A for example.

Figure 7:
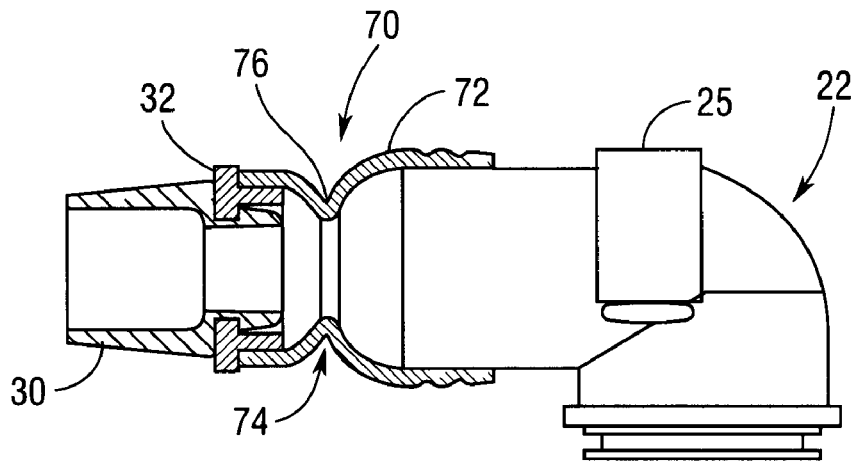
FIG. 7 is a cross-sectional view of a connector according to the principles of another embodiment of the present invention connected to a mask elbow.
Figure 8:
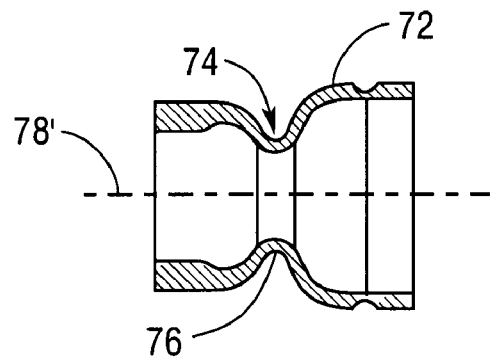
FIG. 8 is a cross-sectional view of the flexible coupling of FIG. 7.

In the embodiment illustrated in FIGS. 7-8, connector 70 is similar to that illustrated in FIGS. 1-5. Mask connection portion 72, however, has a narrowed neck portion 74 forming a flexible joint or living hinge. Narrowed neck portion 74 provides a design which is both simple and robust. Narrowed neck portion 74 forms an inward bellows portion 76, which is generally perpendicular to a central axis 78' (FIG. 8) of connector 70 (as opposed to parallel with center axis 78 as shown in FIG. 3). Narrowed neck portion 74 allows connector 70 to both flex about the central axis 78' of the mask connection portion 72 and move longitudinally. Mask connection portion 72 is preferably formed from an injection molding with TPE or liquid injection molding with silicone resulting in a moderate softness, approximately 60 Shore A for example.

Although taking a slightly different approach, connector 90 illustrated in FIG. 9 is similar to that illustrated in FIGS. 1-5. Connector 90 is a two-piece design having flexible mask connection portion 92 and delivery conduit portion 94. Thus, connector 90 has less structure or geometric form than the connectors described in the previous embodiments. Delivery conduit portion 94 includes a locating groove 96 and a shoulder portion 98. Mask connection portion 92 has a reduced diameter portion 99 which is insertable in groove 96. Connector 90, as illustrated in FIG. 9, does not swivel. The addition of a swivel connector, such as swivel connector 28 discussed above, however is contemplated. Generally, connector 90 is formed from a relatively softer or more elastic material such as low modulus TPE or gel to form a damper to isolate delivery conduit 14 and mask connection portion 92.

Figure 10:
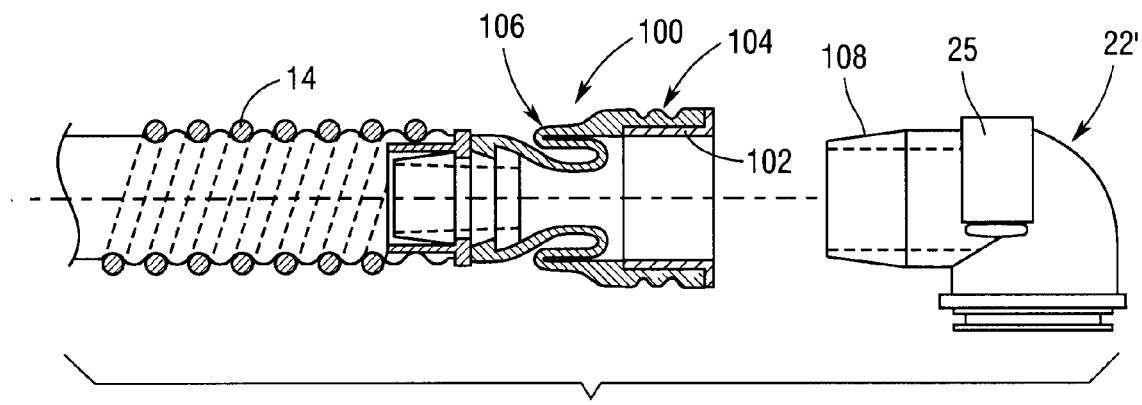
FIG. 10 is a cross-sectional, partially exploded view of a connector according to the principles of another embodiment of the present invention connected to a mask elbow and a delivery conduit.

In the embodiment illustrated in FIG. 10, connector 100 is similar to that illustrated in FIGS. 1-5. Connector 100, however, includes a rigid connector insert 102 in mask connection end 104 of mask connection portion 106. Rigid connector insert 102 is either inserted as a separate element or over molded to mask connection end 104. Rigid connector insert 102 provides conical engagement with elbow 22' and has a frusta-conical inner diameter which corresponds to a frusta-conical-shaped connector end 108 of elbow 22'. Accordingly, connector 100 can be quickly connected with and disconnected from elbow 22'. In this case, a quick connection and disconnection may be achieved through devices such as a finger-lock. Although not illustrated, a swivel connector may be incorporated between rigid connector insert 102 and elbow 22'.

Figure 11:
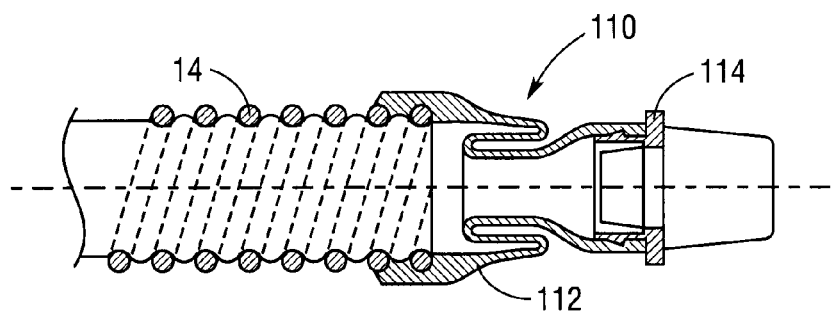
FIG. 11 is a cross-sectional view of a connector according to the principles of another embodiment of the present invention connected to a delivery conduit.

In the embodiment illustrated in FIG. 11, connector 110 is similar to that illustrated in FIGS. 1-5. A flexible coupling 112, however, is connected to delivery conduit 14 and a swivel connector 114 is connectable to, for example, an elbow (not shown) attached to a patient interface device. As a result, connector 110 can be quickly connected with and disconnected from the elbow.

Figure 12:
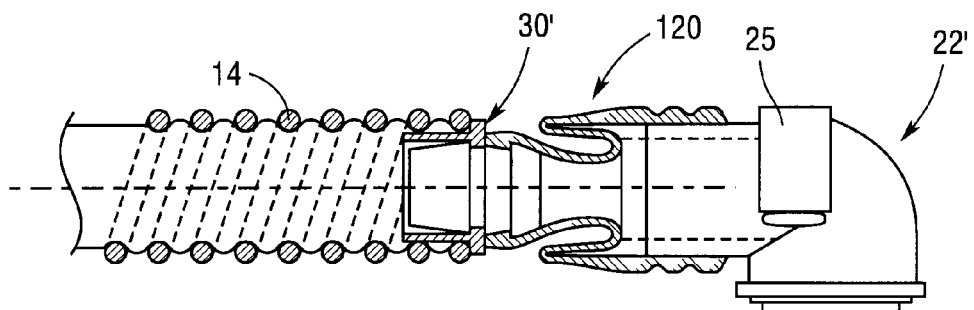
FIG. 12 is a cross-sectional view of a connector according to the principles of another embodiment of the present invention connected to a mask elbow and a delivery conduit.

In the embodiment illustrated in FIG. 12, connector 120 is similar to that illustrated in FIGS. 1-5 except that delivery conduit portion 30' does not include a swivel connector.

FIGS. 13-14 and 15-16 illustrate alternate configurations for a flexible connector. Connector 130, 150 include multiple corrugations which allow connector 130, 150 to both flex about central axis 78", 78'" and move longitudinally. Connector 130 has flat plate style corrugations which are structured to allow connector 130 to flex in the axial direction relative to center line 78" while preventing collapse and/or kinking. Connector 150 has hollow ridge style corrugations which are structured to allow connector 150 to flex in the axial direction relative to center line 78'" while preventing collapse and/or kinking. Both the flat plate style and hollow ridge style corrugations prevent flexible connectors 130, 150 from collapsing and/or kinking when bent. Other types or styles of corrugations may be used while remaining within the scope of the present invention. Connectors 130, 150 have a mask connection end 52', 52" and a conduit connection end 46', 46". Although not illustrated in FIGS. 13-14 and 15-16, connectors 130, 150 may include a swivel connector, such as two-piece swivel connector 28 illustrated in FIG. 2.

Figure 17:
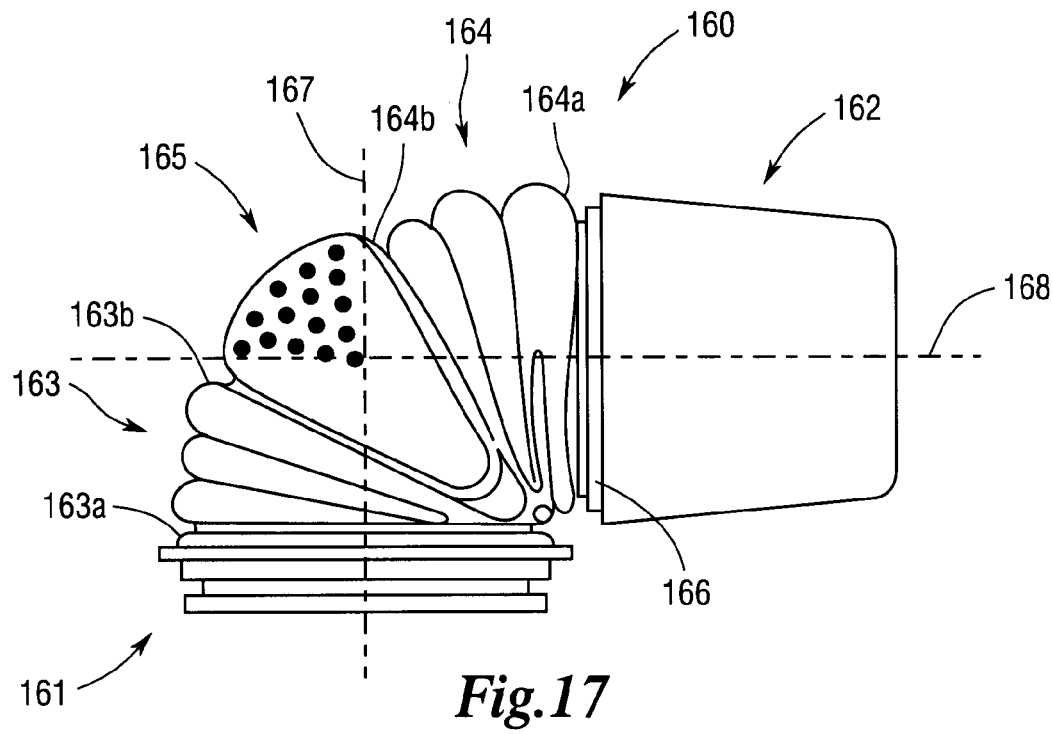
FIG. 17 is a side view of a connector according to the principles of another embodiment of the present invention.

FIGS. 17-22 illustrate various embodiments of connectors, according to the principles of the present invention, which are structured couple with shell 24 of patient interface device 20; thereby eliminating the need for elbow 22, 22'. Referring to FIG. 17, for example, connector 160 includes a mask connection end 161, structured to rotatably couple with shell 24, and a conduit connection end 162 structured to couple with conduit 14. Connector 160 also includes a first flexible coupling 163, with a first end 163a and a second end 163b; a second flexible coupling 164, with a first end 164a and a second end 164b; and an exhaust member 165 structured to allow an exhaust path for the patient's exhaled breath. In this arrangement, first end 163a of first flexible coupling 163 is attached to mask connection end 161, and second end 163b of first flexible coupling 163 is attached to exhaust member 165. In addition, first end 164a of second flexible coupling 164 is attached to conduit connection end 162, while second end 164b of second flexible coupling 164 is attached to exhaust member 165. In this manner, exhaust member 165 is disposed or positioned in-line with respect to connector 160. First flexible coupling 163 and second flexible coupling 164 each include a number of bellows or folds. The bellows may include longitudinally directed inward bellows, corrugations, and/or a narrowed neck portion.

Connector 160 also includes a swivel connector 166, for example as shown in FIG. 17, attached between second flexible coupling 164 and conduit connection end 162. It is contemplated that swivel connector 166 may be re-located on connector 160 while remaining within the scope of the present invention. For example, and without limitation, swivel connector 166 may be located between first flexible coupling 163 and mask connection end 161. Mask connection end 161 and swivel connector 166 provide greater freedom of movement for conduit 14 relative to patient interface device 20. More specifically, mask connection end 161 (when coupled with mask shell 24) is structured to allow connector 160 to rotate about central axis 167 relative to mask shell 24 (not shown), whereas swivel connector 166 is structured to allow connector 116 to rotate about central axis 168 relative to conduit 14 (not shown).

Figure 18:
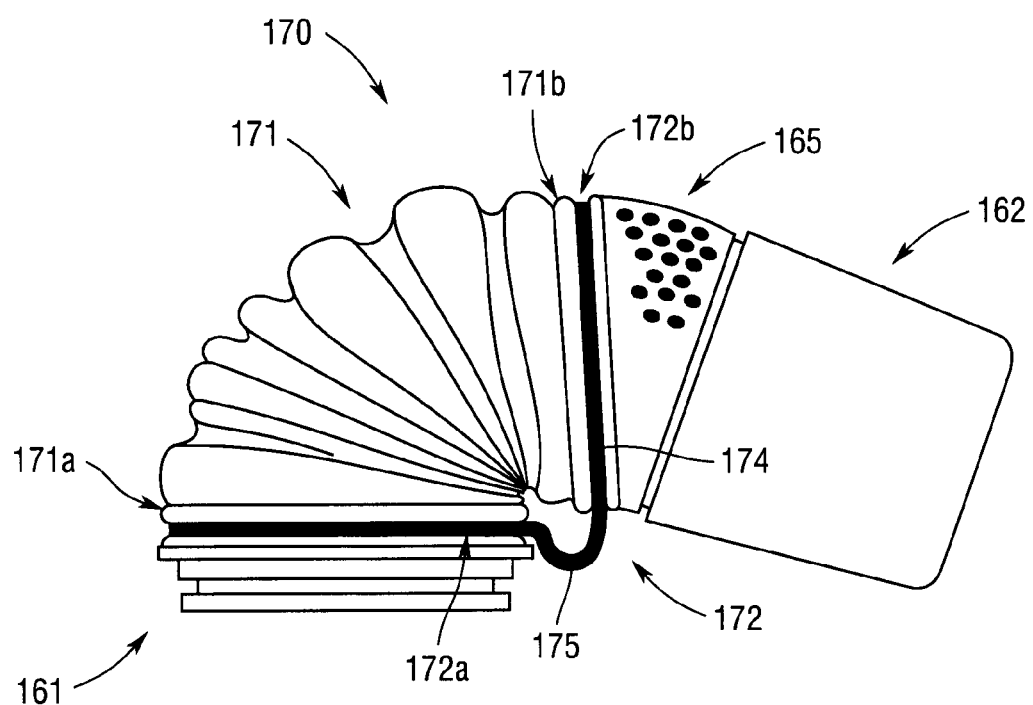
FIG. 18 is a side view of a connector according to the principles of another embodiment of the present invention.
Figure 19:
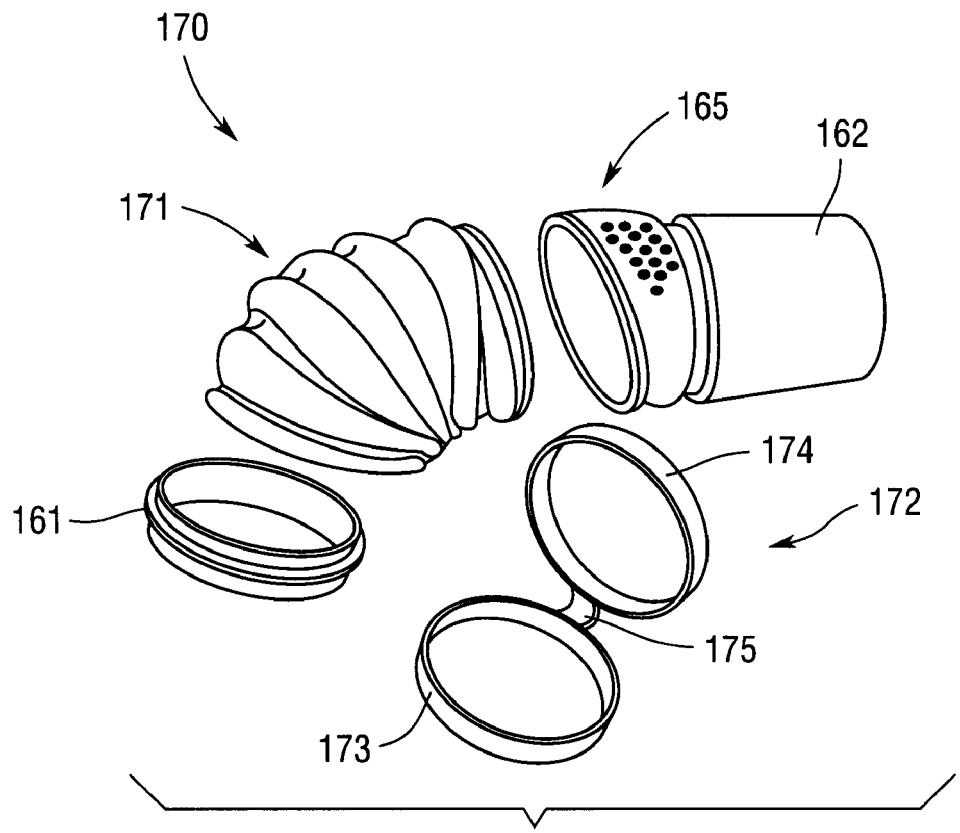
FIG. 19 illustrates the connector of FIG. 18 in a disassembled state.

Referring to FIGS. 18-19, a connector 170 according to an alternative embodiment is illustrated. As discussed above in conjunction with FIG. 17, connector 170 includes a mask connection end 161 and a conduit connection end 162. The arrangement of exhaust member 165 for connector 170, however, is different than that of connector 160. More specifically, exhaust member 165 is located between a single flexible coupling 171 and conduit connector end 162. It is also contemplated that exhaust member 165 may be located between flexible coupling 171 and mask connection end 161. Regardless of the variation, the function of exhaust member 165 remains the same, namely to allow an exhaust path for the patient's exhaled breath. Flexible coupling 171 includes a number of bellows or folds. The bellows may include longitudinally directed inward bellows, corrugations, and/or a narrowed neck portion. Although connector 170 is illustrated without a swivel connector 166, it is contemplated that swivel connector 166 may be added to connector 170 while remaining within the scope of the present invention.

Additionally, connector 170 includes a hinge element 172 which is in operable communication with flexible coupling 171 and is used to define the range of movement for flexible coupling 171. Hinge element 172 includes a first end 172a and a second end 172b. In the current embodiment, first end 172a of hinge element 172 is attached to mask connection end 161 and/or a first end 171a of flexible coupling 171, and second end 172b of hinge element 172 is attached to conduit connector end 162 and/or a second end 171b of flexible coupling 171. As a result, an amount of movement is allowed through flexible coupling 171; however, this movement is specifically limited in certain directions and angles by hinge element 172. Generally, hinge element 172 is constructed of a flexible or semi rigid material having less flexibility than the flexible coupling 171. Hinge element 172 may be constructed, for example, from TPE, higher durometer silicone (e.g., greater than or equal to 70 Shore A), and/or a thermoplastic polyester elastomer (i.e. Hytrel™ manufactured by Du Pont).

Hinge element 172 includes a first retaining ring 173 and a second retaining ring 174. In particular, first end 172a of hinge element 172 is the first retaining ring 173, while second end 172b of hinge element 172 is the second retaining ring 174. First retaining ring 173 and second retaining ring 174 are connected by an elbow joint 175. Not only does such an arrangement allow for the appropriate limitation of movement, it also provides a default rest position, which can be defined through the resting structure or default position of hinge element 172.

Figure 20:
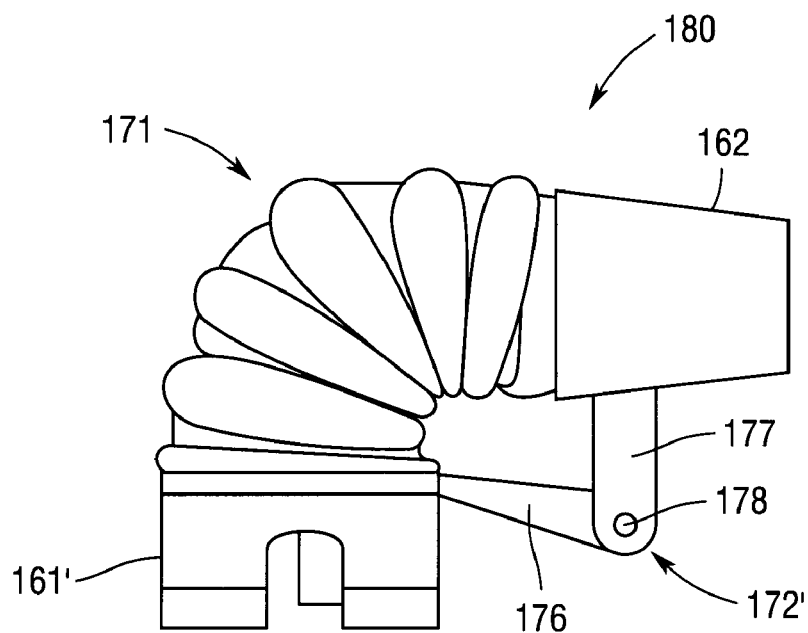
FIG. 20 is a side view of a connector according to the principles of another embodiment of the present invention.

A connector 180 with a hinge element 172' structured to impart further restrictions upon the range of movement of flexible coupling 171 is illustrated in FIG. 20. Connector 180 includes a mask connection end 161' structured to rotatably couple with mask shell 24 and a conduit connection end 162. Additionally, connector 180 includes a hinge element 172' having a first end 172a' (illustrated as a first arm 176) and a second end 172b' (illustrated as a second arm 177). In this embodiment, first arm 176 and second arm 177 are movably connected at a hinge point 178, such that hinge element 172' can be rotated about hinge point 178, thereby defining a range of movement.

Although not shown in FIG. 20, connector 180 may also include a swivel connector 166. For example, swivel connector 166 may be attached between flexible coupling 171 and mask connection end 161 and/or connected between flexible coupling 171 and conduit connection end 162. Such a swivel arrangement provides for even greater range of movement and twisting of the various components and subcomponents of the structure.

In order to better define the range of movement, hinge element 172, 172' can be made from a substantially flexible material, as in the case of retaining rings 173, 174 in FIGS. 18 and 19, or as a substantially rigid material, for example, arms 176, 177 illustrated in FIG. 20. Of course, the use of a rigid material provides a much more limited and definable range of movement along a specific axis, and virtually eliminates substantial lateral movement.

Figure 21:
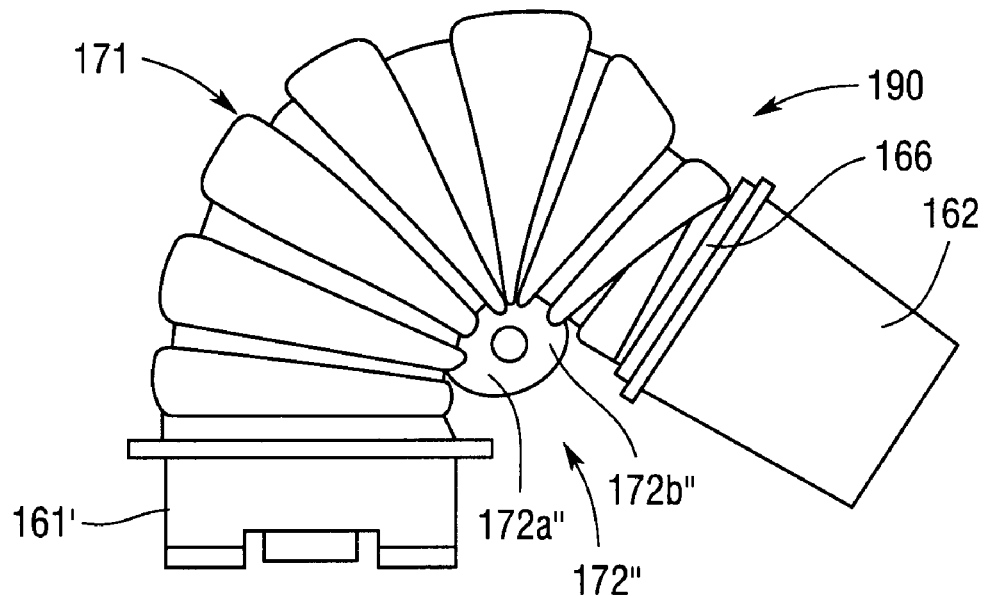
FIG. 21 is a side view of a connector according to the principles of another embodiment of the present invention.
Figure 22:
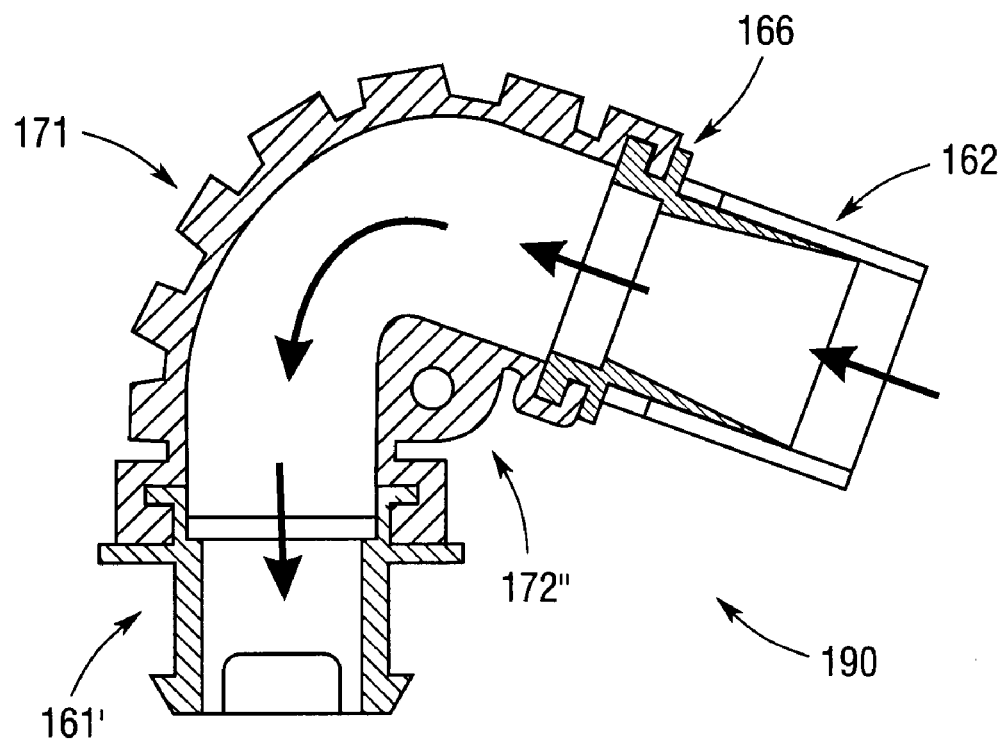
FIG. 22 is a side, sectional view of the connector of FIG. 21.

A connector 190 according to yet another embodiment is illustrated in FIGS. 21 and 22. In this embodiment, hinge element 172" is considered a "living hinge" and is in operable communication with flexible coupling 171 for defining the range of movement of flexible coupling 171. Hinge element 172" is a unitary piece hinge. In particular, hinge element 172" has a first end 172a" and a second end 172b". First end 172" of hinge element 172" is attached to a portion of flexible coupling 171 and second end 172" of hinge element 172" is attached to another portion of flexible coupling 171. In this manner, flexible coupling 171 is held in the form of an elbow.

Further, it may be desirable to hold flexible coupling 171 at an acute angle, as seen in FIG. 21. Hinge element 172" may be made of a flexible material, and further may be molded to or molded with, such as integrally formed with, flexible coupling 171. Therefore, hinge element 172" and flexible coupling 171 can be formed from the same material. For example, connector 190 can be made in an injection mold process from a variety of materials that are moldable. Still further, the flexible material can be an elastomer, a polymer, a thermoplastic material, a molded material, a moldable material, a synthetic material, etc.

The patient interface device 20 of any or all of the embodiments of the present invention communicates a flow of breathing gas to the patient's airway from a pressure generating device 12, such as a ventilator, CPAP device, or variable pressure device, e.g., an auto-titrating pressure support device or a BiPAP device manufactured and distributed by Respironics, Inc. of Pittsburgh, Pa., in which the pressure provided to the patient varies with the patient's respiratory cycle so that a higher pressure is delivered during inspiration than during expiration or an auto-titratition pressure support system where the pressure varies with the condition of the patient, such as whether the patient is snoring or experiencing an apnea or hypopnea.

The present invention contemplates that exhaust member 165 can have any configuration, so long as the function of exhausting a sufficient amount of gas to atmosphere is achieved. For example, the exhaust member can be configured to provide a continuous flow rate for the venting of exhaust gas to atmosphere, or can be configured to provide a variable flow rate; dependent, for example, on the pressure of the gas in the closed system.

In the illustrated embodiment, exhaust member 165 is defined by a plurality of vent holes provided in the wall thereof. The number, size, hole pattern, and shape of the holes can have any configuration. One example of a multiple-hole type of exhaust member or assembly suitable for use in the present invention is disclosed in U.S. patent application Ser. No. 10/119,673 (Pub. No. 2003/0005931), the contents of which are incorporated herein by reference. It should also be noted that only one exhaust member or assembly need be provided on the mask, so long as the exhaust flow rate is sufficient to provide an adequate exhaust gas venting function. The exhaust member can also be omitted if exhausting gas from the system is not needed or if the exhaust member is provided elsewhere, such as in the patient circuit.

It is contemplated that additional features may be incorporated into one or more of the embodiments discussed above and/or incorporated into a combination of one or more of the embodiments discussed above. For example, exhaust member 165 may be incorporated into one or more of the flexible connectors illustrated in FIGS. 1-16. It is also contemplated that the exhaust function may be accomplished by placing a number of exhaust ports directly through a portion of the flexible material, for example and without limitation, directly through mask connection portion 26.

Figure 23:
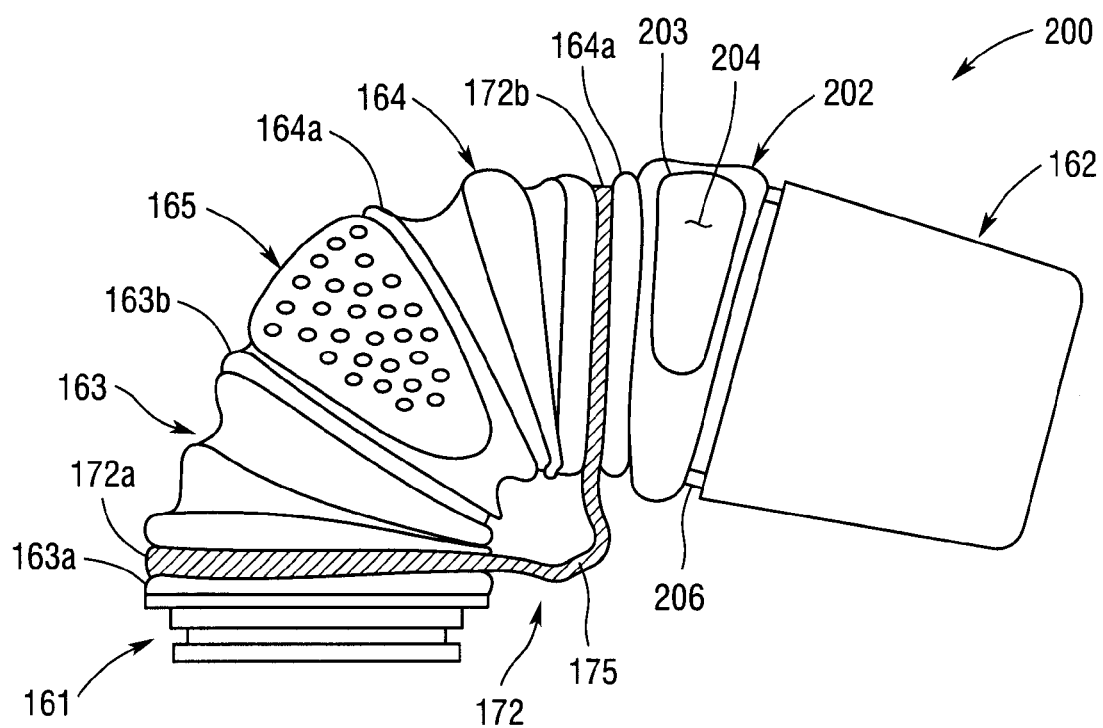
FIG. 23 is a side view of a connector according to the principles of another embodiment of the present invention.

As yet another example, FIG. 23 illustrates a flexible connector 200 which incorporates a number of features from flexible connector 160 of FIG. 17, a number of features from flexible connector 170 of FIG. 18, and additional features not previously discussed. More specifically, flexible connector 120 includes mask connection end 161, conduit connection end 162, first flexible coupling 163 (with first end 163a and second end 163b), second flexible coupling 164 (with first end 164a and second end 164b), and exhaust member 165. Connector 200 also includes hinge element 172 structured to define the range of movement for flexible couplings 163 and 164.

Additionally, connector 200 also includes an entrainment valve 202 and associated spacer 206 incorporated between first end 164a of second flexible coupling 164 and conduit connection end 162. In the embodiment illustrated in FIG. 23, entrainment valve 202 includes an opening 203 which is generally occluded by flap 204 when a flow of breathing gas is being delivered to the patient's airway from a pressure generating device 12. Entrainment valve 202 is structured such that opening 203 is generally open (i.e., flap 204 does not fully occlude opening 203) should the flow of breathing gas be interrupted. As a result, the patient is supplied with ambient air should the flow of breathing gas be interrupted.

Examples of other entrainment valves suitable for use in the present invention are disclosed in U.S. Pat. Nos. 5,438,981, 5,647,355, and 6,851,425, the contents of which are incorporated herein by reference. Although illustrated separated components, it is contemplated that exhaust member 165 and Entrainment valve 202 may be combined into a single assembly. One example of an exhaust member/entrainment valve combination is suitable for use in the present invention is disclosed in U.S. patent application Ser. No. 11/312,027 (Pub. No. 2003/0005931), the contents of which are incorporated herein by reference.

Spacer 206 is structured to provide a swivel connection between mask connection end 162 and entrainment valve 202. In the current embodiment, spacer 206 is structured so as to reduce friction during the rotation of entrainment valve 202 relative to mask connection end 162.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A connector structured to connect a delivery conduit to a patient interface device comprising:
   (a) a flexible coupling comprising:
      (1) a first end,
      (2) a second end, and
      (3) a bellows portion extending radially with respect to a central axis between the first end and the second end, the bellows portion having a longitudinally directed inward bellows disposed parallel to the central axis when the flexible coupling is in a non-flexed state; and (b) a swivel connector connected to the flexible coupling.

2. The connector of claim 1, wherein the first end of the flexible coupling is structured to connect with a first end of the swivel connector, wherein the second end of the flexible coupling is structured to connect with the delivery conduit, and wherein a second end of the swivel connector is structured to connect with the patient interface device.

3. The connector of claim 1, wherein the first end of the flexible coupling is structured to connect with a first end of the swivel connector, wherein the second end of the flexible coupling is structured to connect with the patient interface device, and wherein a second end of the swivel connector is structured to connect with the delivery conduit.

4. The connector of claim 1, wherein the bellows portion has a curved S-shape cross-section.

5. The connector of claim 1, wherein the bellows portion has a narrowed neck portion.

6. The connector of claim 1, wherein the bellows portion has a plurality of corrugations.

7. The connector of claim 1, further comprising an exhaust member structured to allow an exhaust path for a patient's exhaled breath.

8. The connector of claim 1, further comprising a hinge element structured to limit an amount of movement of the flexible coupling.

9. The connector of claim 1, further comprising an entrainment valve structured to supply a patient with ambient air should a flow of breathing gas being delivered to such patient be interrupted.

10. A connector structured to connect a delivery conduit to a patient interface device comprising:

(a) a flexible coupling comprising:
   (1) a first end,
   (2) a second, and
   (3) a bellows portion extending radially with respect to a central axis between the first end and the second end, wherein the bellows portion includes a longitudinally directed inward bellows disposed parallel to the central axis when the flexible coupling is in a non-flexed state; and (b) (1) hinge clement structured to limit an amount of movement of the flexible, coupling, (2) an entrainment valve structured to supply a patient with ambient air should a flow of breathing gas being delivered to the patient be interrupted, or (3) both the hinge element and the entrainment valve.

11. The connector of claim 10, wherein the flexible coupling is structured to connect with at least one of the delivery conduit and the patient interface device.

12. The connector of claim 11, further comprising a swivel connector structured to connect with the flexible coupling.

13. The connector of claim 12, wherein the first end of the flexible coupling is structured to connect with a first end of the swivel connector, wherein the second end of the flexible coupling is structured to connect with the delivery conduit, and wherein a second end of the swivel connector is structured to connect with the patient interface device.

14. The connector of claim 12, wherein the first end of the flexible coupling is structured to connect with a first end of the swivel connector, wherein the second end of the flexible coupling is structured to connect with the patient interface device, and wherein a second end of the swivel connector is structured to connect with the delivery conduit.

15. The connector of claim 12, further comprising an exhaust member structured to allow an exhaust path for the patient's exhaled breath.

16. The connector of claim 10, wherein the bellows has a curved S-shape cross-section.

17. A system for delivering a pressurized breathing gas to a patient, comprising:

(a) a patient interface device;

(b) a gas flow generating device structure to produce a flow of gas;

(c) a delivery conduit having a first end portion operatively coupled to the gas flow generating device and a second end portion, wherein the delivery conduit is structured to carry the flow of gas from the gas flow generating device during operation of the system; and (d) a connector structured to connect the delivery conduit to the patient interface device, the connector comprising:
   (1) a flexible coupling comprising:
      (i) a first end,
      (ii) a second end, and
      (iii) a bellows portion extending radially with respect to a central axis between the first end and the second end, the bellows portion having a longitudinally directed inward bellows disposed parallel to the central axis when the flexible coupling is in a non-flexed state; and
   (2) a swivel connector connected to the flexible coupling.

18. The system of claim 17, wherein the first end of the flexible coupling is structured to connect with a first end of the swivel connector, wherein the second end of the flexible coupling is structured to connect with the delivery conduit, and wherein a second end of the swivel connector is structured to connect with the patient interface device.

19. The system of claim 17, wherein the first end of the flexible coupling is structured to connect with a first end of the swivel connector, wherein the second end of the flexible coupling is structured to connect with the patient interface device, and wherein a second end of the swivel connector is structured to connect with the delivery conduit.

20. The system of claim 17, wherein the bellows portion has a curved S-shape cross-section.

21. The system of claim 17, wherein the bellows portion has a narrowed neck portion.

22. The system of claim 17, wherein the bellows portion has a plurality of corrugations.

23. The system of claim 17, wherein the connector further comprises an exhaust member structured to allow an exhaust path for the patient's exhaled breath.

24. The system of claim 17, wherein the connector further comprises a hinge element structured to limit an amount of movement of the flexible coupling.

25. The system of claim 17, wherein the connector further comprises an entrainment valve structured to supply the patient with ambient air should the flow of gas be interrupted.

26. The connector of claim 4, wherein the S-shape cross section has outer portions and a lower interior curve therebetween, and wherein the bellows portion has a thickness that gradually reduces from a maximum thickness at the outer portions to a minimum thickness at the lower interior curve.

* * * * *